(12) United States Patent
Dumousseaux et al.

(10) Patent No.: US 9,023,328 B2
(45) Date of Patent: May 5, 2015

(54) W/O EMULSION WITH EMULSIFYING SILICONE ELASTOMER AND VOLATILE LINEAR ALKANE

(75) Inventors: Christophe Dumousseaux, Antony (FR); Valerie Dique-Mouton, Chevilly Larue (FR)

(73) Assignee: L'Oreal, Paris (FR)

( * ) Notice: Subject to any disclaimer, the term of this patent is extended or adjusted under 35 U.S.C. 154(b) by 40 days.

(21) Appl. No.: 12/969,615

(22) Filed: Dec. 16, 2010

(65) Prior Publication Data

US 2011/0150800 A1 Jun. 23, 2011

Related U.S. Application Data

(60) Provisional application No. 61/290,965, filed on Dec. 30, 2009.

(30) Foreign Application Priority Data

Dec. 18, 2009 (FR) .................... 09 59218

(51) Int. Cl.
| | | |
|---|---|---|
| *A61K 8/18* | (2006.01) | |
| *A61K 8/06* | (2006.01) | |
| *A61K 8/31* | (2006.01) | |
| *A61K 8/894* | (2006.01) | |
| *A61K 8/895* | (2006.01) | |
| *A61Q 1/02* | (2006.01) | |

(52) U.S. Cl.
CPC . *A61K 8/06* (2013.01); *A61K 8/064* (2013.01); *A61K 8/31* (2013.01); *A61K 8/894* (2013.01); *A61K 8/895* (2013.01); *A61Q 1/02* (2013.01)

(58) Field of Classification Search
None
See application file for complete search history.

(56) References Cited

U.S. PATENT DOCUMENTS

| | | | | |
|---|---|---|---|---|
| 6,162,421 | A * | 12/2000 | Ordino et al. | 424/64 |
| 7,858,104 | B2 * | 12/2010 | Simonnet et al. | 424/400 |
| 2006/0293431 | A1 * | 12/2006 | Kani et al. | 524/492 |
| 2008/0269352 | A1 | 10/2008 | Falkowski et al. | |
| 2010/0015073 | A1 * | 1/2010 | Clavel et al. | 424/63 |

FOREIGN PATENT DOCUMENTS

| | | |
|---|---|---|
| DE | 10 2008 012 457 | 12/2008 |
| EP | 1 068 851 | 1/2001 |
| EP | 1 932 505 | 6/2008 |
| WO | WO 2007/064687 | 6/2007 |

OTHER PUBLICATIONS

French Search Report issued Aug. 19, 2010, in FR 09 59218, filed Dec. 18, 2009.
M. Starch et al., "New Developments in Silicone Elastomers for Skin Care," Dow Corning brochure, Oct. 30, 2007, XP002597215.
KSG Series, "15-16-18-41-42-43-44-210-310-320-330-340-7-10-830-840," Product Brochure Shinetsu, Jan. 1, 2004, pp. 2, 7-9, 11. XP002424955.
Notice of Reasons for Rejections in corresponding Japanese Application No. 2010-281917, dated Jan. 26, 2015.

* cited by examiner

*Primary Examiner* — Anand Desai
*Assistant Examiner* — Melissa Mercier
(74) *Attorney, Agent, or Firm* — Oblon, McClelland, Maier & Neustadt, L.L.P.

(57) ABSTRACT

Composition particularly useful for caring for and/or making up keratin materials, in particular the skin, in the form of a water-in-oil emulsion containing water and:
(i) at least one or more, in particular $C_7$-$C_{14}$, volatile linear alkane(s), and
(ii) at least one emulsifying silicone elastomer.

19 Claims, No Drawings

W/O EMULSION WITH EMULSIFYING SILICONE ELASTOMER AND VOLATILE LINEAR ALKANE

REFERENCE TO PRIOR APPLICATIONS

This application claims priority to U.S. provisional application Ser. No. 61/290,965, filed Dec. 30, 2009; and to French patent application 09 59218, filed Dec. 18, 2009, both incorporated herein by reference.

FIELD OF THE INVENTION

The subject of the present invention is a care and/or makeup composition in the form of a water-in-oil emulsion containing an emulsifying silicone elastomer and one or more linear volatile alkane(s). Such a composition simultaneously exhibits good stability, a fluid nature, easy application and a soft and matting final result.

BACKGROUND OF THE INVENTION

Care and/or makeup compositions, in particular foundations, are provided in the form of varied textures ranging from fluid to solid.

Consumers find fluid textures attractive because they are easy to apply and give the feeling of a thin film and a light and natural finish which is forgotten after application.

It is nevertheless difficult to obtain fluid textures in the form of water-in-oil emulsions, with a high content of aqueous phase, desired for its freshness and moisturization benefits and nongreasy effect, which tends towards thickening the composition. Moreover, fluid textures, in particular when they contain pulverulent materials, in particular high-density particles (for example: pigments, inorganic fillers) exhibit problems of stability over time. In addition, when the product is intended to provide mattness and fastness and when it contains a high level of pulverulent materials and, optionally, the presence of a film-forming agent, the drying time is generally very short, which prevents the product from being worked on the skin for a sufficiently long period of time.

It therefore appears to be of interest to be able to develop matting care and/or makeup compositions which ally good fluidity and good stability and which can be worked on the skin for a long time, giving a soft and matting finish.

DETAILED DESCRIPTION OF THE PREFERRED EMBODIMENTS

The inventors have found, surprisingly, that the use of one or more volatile linear $C_7$-$C_{14}$ alkanes, in particular with a flashpoint>70° C., makes it possible to fluidify a composition containing an emulsifying silicone elastomer, even with a very high level of aqueous phase (aqueous phase/liquid fatty phase ratio>1). The combination according to the invention therefore makes it possible to formulate fluid water-in-oil emulsions with a high level of aqueous phase.

The inventors have, moreover, shown that the use of one or more volatile linear alkanes, in particular with a flashpoint>70° C., and of at least one emulsifying silicone elastomer, makes it possible to obtain a product containing pulverulent materials with good fluidity, good stability, good application properties and a soft and matting effect after application.

According to a first aspect, the subject of the invention is therefore a composition, preferably useful for caring for and/or making up keratin materials, in particular the skin, in the form of a water-in-oil emulsion comprising, in a physiologically acceptable medium:
 (i) at least one or more, in particular $C_7$-$C_{14}$, volatile linear alkane(s),
 (ii) at least one emulsifying silicone elastomer.

According to a first preferred embodiment, the invention relates to a composition for caring for and/or making up keratin materials, in particular the skin, in the form of a water-in-oil emulsion comprising, in a physiologically acceptable medium:
 (i) at least one or more, in particular $C_7$-$C_{14}$, volatile linear alkane(s),
 (ii) at least one emulsifying silicone elastomer, and
 (iii) at least 10% by weight of pulverulent materials, relative to the total weight of said composition.

According to another embodiment, the invention relates to a cosmetic composition for caring for and/or making up keratin materials, in particular the skin, in the form of a water-in-oil emulsion comprising, in a physiologically acceptable medium:
 (i) at least one or more, in particular $C_7$-$C_{14}$, volatile linear alkane(s), and
 (ii) at least one emulsifying silicone elastomer, and
wherein the aqueous phase/liquid fatty phase ratio is greater than 1.

According to another embodiment, the invention relates to a cosmetic composition for caring for and/or making up keratin materials, in particular the skin, in the form of a water-in-oil emulsion comprising, in a physiologically acceptable medium:
 (i) at least one or more, in particular $C_7$-$C_{14}$, volatile linear alkane(s),
 (ii) at least one emulsifying silicone elastomer, and
 (iii) at least 10% by weight of pulverulent materials, relative to the total weight of said composition, and
wherein the aqueous phase/liquid fatty phase ratio is greater than 1.

The present invention is also directed towards a cosmetic process for caring for and/or making up keratin materials, in particular the skin, comprising the application of a composition according to the invention.

The composition according to the invention is in the form of a water-in-oil emulsion comprising an aqueous phase dispersed in a liquid fatty phase, and comprises at least one physiologically acceptable medium.

The term "physiologically acceptable medium" is intended to denote a medium that is particularly suitable for the application of a composition of the invention to keratin materials, in particular the skin and the lips.

The physiologically acceptable medium is generally adapted to the nature of the substrate onto which the composition is to be applied, and also to the way in which the composition is to be packaged.

The composition according to the invention comprises at least one or more, in particular $C_7$-$C_{14}$, volatile linear alkanes.

Volatile Linear Alkanes

The composition of the invention may comprise, for example, from 1% to 30%, preferably from 2% to 15%, preferably from 3% to 10% by weight of volatile linear alkanes, relative to the total weight of said composition.

The term "one or more volatile linear alkane(s)" is intended to mean, without distinction, "one or more volatile linear alkane oil(s)".

A volatile linear alkane that is suitable for the invention is liquid at ambient temperature (approximately 25° C.) and at atmospheric pressure (760 mmHg).

The term "volatile linear alkane" that is suitable for the invention is intended to mean a cosmetic linear alkane which is capable of evaporating on contact with the skin in less than one hour, at ambient temperature (25° C.) and atmospheric pressure (760 mmHg, i.e. 101 325 Pa), which is liquid at ambient temperature, in particular having an evaporation rate ranging from 0.01 to 15 mg/cm$^2$/min, at ambient temperature (25° C.) and atmospheric pressure (760 mmHg).

Preferably, the "volatile linear alkanes" that are suitable for the invention have an evaporation rate ranging from 0.01 to 3.5 mg/cm$^2$/min, at ambient temperature (25° C.) and atmospheric pressure (760 mmHg).

Preferably, the "volatile linear alkanes" that are suitable for the invention have an evaporation rate ranging from 0.01 to 1.5 mg/cm$^2$/min, at ambient temperature (25° C.) and atmospheric pressure (760 mmHg).

More preferably, the "volatile linear alkanes" that are suitable for the invention have an evaporation rate ranging from 0.01 to 0.8 mg/cm$^2$/min, at ambient temperature (25° C.) and atmospheric pressure (760 mmHg).

Preferably, the "volatile linear alkanes" that are suitable for the invention have an evaporation rate ranging from 0.01 to 0.3 mg/cm$^2$/min, at ambient temperature (25° C.) and atmospheric pressure (760 mmHg).

More preferably, the "volatile linear alkanes" that are suitable for the invention have an evaporation rate ranging from 0.01 to 0.12 mg/cm$^2$/min, at ambient temperature (25° C.) and atmospheric pressure (760 mmHg).

The evaporation rate of a volatile alkane in accordance with the invention (and more generally of a volatile solvent) may in particular be evaluated by means of the protocol described in WO 06/013413, and more particularly by means of the protocol described below.

15 g of volatile hydrocarbon-based solvent are placed in a crystallizing dish (diameter: 7 cm) placed on a balance that is in a chamber of approximately 0.3 m$^3$ with regulated temperature (25° C.) and hygrometry (50% relative humidity).

The liquid is allowed to evaporate freely, without stirring, while providing ventilation by means of a fan (Papst-Motoren, reference 8550 N, rotating at 2700 rpm) placed vertically above the crystallizing dish containing the volatile hydrocarbon-based solvent, the blades being directed towards the crystallizing dish, 20 cm away from the bottom of the crystallizing dish.

The mass of volatile hydrocarbon-based solvent remaining in the crystallizing dish is measured at regular time intervals.

The evaporation profile of the solvent is then obtained by plotting the curve of the amount of product evaporated (in mg/cm$^2$) as a function of time (in min).

The evaporation rate is then calculated, which corresponds to the tangent to the origin of the curve obtained. The evaporation rates are expressed in mg of volatile solvent evaporated per unit surface area (cm$^2$) and per unit of time (minute).

According to one preferred embodiment, the "volatile linear alkanes" that are suitable for the invention have a non-zero vapour pressure (also known as the saturating vapour pressure), at ambient temperature, in particular a vapour pressure ranging from 0.3 Pa to 6000 Pa.

Preferably, the "volatile linear alkanes" that are suitable for the invention have a vapour pressure ranging from 0.3 to 2000 Pa, at ambient temperature (25° C.)

Preferably, the "volatile linear alkanes" that are suitable for the invention have a vapour pressure ranging from 0.3 to 1000 Pa, at ambient temperature (25° C.)

More preferably, the "volatile linear alkanes" that are suitable for the invention have a vapour pressure ranging from 0.4 to 600 Pa, at ambient temperature (25° C.)

Preferably, the "volatile linear alkanes" that are suitable for the invention have a vapour pressure ranging from 1 to 200 Pa, at ambient temperature (25° C.)

Even more preferably, the "volatile linear alkanes" that are suitable for the invention have a vapour pressure ranging from 3 to 60 Pa, at ambient temperature (25° C.)

According to one embodiment, a volatile linear alkane that is suitable for the invention may have a flashpoint that is in the range of from 30 to 120° C., and more particularly from 40 to 100° C. The flashpoint is in particular measured according to standard ISO 3679.

According to one embodiment, an alkane that is suitable for the invention may be a volatile linear alkane comprising from 7 to 14 carbon atoms.

Preferably, the "volatile linear alkanes" that are suitable for the invention comprise from 8 to 14 carbon atoms.

Preferably, the "volatile linear alkanes" that are suitable for the invention comprise from 9 to 14 carbon atoms.

Preferably, the "volatile linear alkanes" that are suitable for the invention comprise from 10 to 14 carbon atoms.

Preferably, the "volatile linear alkanes" that are suitable for the invention comprise from 11 to 14 carbon atoms.

According to one advantageous embodiment, the "volatile linear alkanes" that are suitable for the invention have an evaporation rate, as defined above, ranging from 0.01 to 3.5 mg/cm$^2$/min at ambient temperature (25° C.) and atmospheric pressure (760 mmHg), and comprise from 8 to 14 carbon atoms.

A volatile linear alkane that is suitable for the invention may advantageously be of plant origin.

Preferably, the volatile linear alkane or the mixture of volatile linear alkanes present in the composition according to the invention comprises at least one $^{14}C$ (carbon-14) carbon isotope. In particular, the $^{14}C$ isotope may be present in a $^{14}C/^{12}C$ ratio of greater than or equal to $1\times10^{-16}$, preferably greater than or equal to $1\times10^{-15}$, more preferably greater than or equal to $7.5\times10^{-14}$, and better still greater than or equal to $1.5\times10^{13}$. Preferably, the $^{14}C/^{12}C$ ratio ranges from $6\times10^{13}$ to $1.2\times10^{12}$.

The amount of $^{14}C$ isotopes in the volatile linear alkane or the mixture of volatile linear alkanes can be determined by methods known to those skilled in the art, such as the Libby counting method, liquid scintillation spectrometry or accelerator mass spectrometry.

Such an alkane can be obtained, directly or in several steps, from a plant starting material such as an oil, a butter, a wax, etc.

As examples of alkanes that are suitable for the invention, mention may be made of the alkanes described in patent applications WO 2007/068371 or WO 2008/155059 by the company Cognis (mixtures of different alkanes differing by at least one carbon). These alkanes are obtained from fatty alcohols, which are themselves obtained from coconut oil or palm oil.

By way of example of linear alkanes that are suitable for the invention, mention may be made of n-heptane ($C_7$), n-octane ($C_8$), n-nonane ($C_9$), n-decane ($C_{10}$), n-undecane ($C_{11}$), n-dodecane ($C_{12}$), n-tridecane ($C_{13}$) and n-tetradecane ($C_{14}$), and mixtures thereof. According to one particular embodiment, the volatile linear alkane is chosen from n-nonane, n-undecane, n-dodecane, n-tridecane and n-tetradecane, and mixtures thereof.

According to one preferred embodiment, mention may be made of mixtures of n-undecane ($C_{11}$) and of n-tridecane ($C_{13}$), obtained in Examples 1 and 2 of application WO 2008/155059 by the company Cognis.

Mention may also be made of n-dodecane ($C_{12}$) and n-tetradecane ($C_{14}$), sold by Sasol under the references, respectively, Parafol 12-97 and Parafol 14-97, and also mixtures thereof.

The volatile linear alkane may be used alone.

Alternatively or preferentially, a mixture of at least two different volatile linear alkanes, differing from one another by a carbon number n of at least 1, in particular differing from one another by a carbon number of 1 or 2, may be used.

According to a first embodiment, a mixture of at least two different volatile linear alkanes comprising from 10 to 14 carbon atoms and differing from one another by a carbon number of at least 1 is used. By way of examples, mention may in particular be made of mixtures of $C_{10}/C_{11}$, $C_{11}/C_{12}$ or $C_{12}/C_{13}$ volatile linear alkanes.

According to another embodiment, a mixture of at least two different volatile linear alkanes comprising from 10 to 14 carbon atoms and differing from one another by a carbon number of at least 2 is used. By way of examples, mention may in particular be made of mixtures of $C_{10}/C_{12}$ or $C_{12}/C_{14}$ volatile linear alkanes, for an even carbon number n, and the $C_{11}/C_{13}$ mixture for an odd carbon number n.

According to one preferred embodiment, a mixture of at least two different volatile linear alkanes comprising from 10 to 14 carbon atoms and differing from one another by a carbon number of at least 2, and in particular a mixture of $C_{11}/C_{13}$ volatile linear alkanes or a mixture of $C_{12}/C_{14}$ volatile linear alkanes, is used.

Other mixtures combining more than 2 volatile linear alkanes according to the invention, for instance a mixture of at least 3 different volatile linear alkanes comprising from 7 to 14 carbon atoms and differing from one another by a carbon number of at least 1, also form part of the invention, but mixtures of 2 volatile linear alkanes according to the invention are preferred (binary mixtures), said 2 volatile linear alkanes preferably representing more than 95%, and better still more than 99%, by weight of the total content of volatile linear alkanes in the mixture.

According to one particular embodiment of the invention, in a mixture of volatile linear alkanes, the volatile linear alkane having the smallest carbon number is predominant in the mixture.

According to another embodiment of the invention, a mixture of volatile linear alkanes in which the volatile linear alkane having the largest carbon number is predominant in the mixture is used.

By way of examples of mixtures that are suitable for the invention, mention may in particular be made of the following mixtures:
  from 50% to 90% by weight, preferably from 55% to 80% by weight, more preferably from 60% to 75% by weight of $C_n$ volatile linear alkane, with n ranging from 7 to 14,
  from 10% to 50% by weight, preferably from 20% to 45% by weight, preferably from 24% to 40% by weight, of $C_{n+x}$ volatile linear alkane, with x greater than or equal to 1, preferably x=1 or x=2, with n+x between 8 and 14,
  relative to the total weight of the alkanes in said mixture.

In particular, said mixture of alkanes according to the invention contains:
  less than 2% by weight, preferably less than 1% by weight of branched hydrocarbons,
  and/or less than 2% by weight, preferably less than 1% by weight of aromatic hydrocarbons,
  and/or less than 2% by weight, preferably less than 1% by weight and preferentially less than 0.1% by weight of unsaturated hydrocarbons in the mixture.

More particularly, a volatile linear alkane that is suitable for the invention may be used in the form of an n-undecane/n-tridecane mixture.

In particular, use will be made of a mixture of volatile linear alkanes comprising:
  from 55% to 80% by weight, preferably from 60% to 75% by weight of $C_{11}$ volatile linear alkane (n-undecane),
  from 20% to 45% by weight, preferably from 24% to 40% by weight of $C_{13}$ volatile linear alkane (n-tridecane)
  relative to the total weight of the alkanes in said mixture.

According to one particular embodiment, the mixture of alkanes is an n-undecane/n-tridecane mixture. In particular, such a mixture can be obtained according to Example 1 or Example 2 of WO 2008/155059.

According to another particular embodiment, the n-dodecane sold under the reference Parafol 12-97 by Sasol is used.

According to another particular embodiment, the n-tetradecane sold under the reference Parafol 14-97 by Sasol is used.

According to yet another embodiment, a mixture of n-dodecane and of n-tetradecane is used.

According to one particular embodiment of the invention, the composition may comprise less than 15% by weight, or even less than 10% by weight, or even less than 5% by weight, or even may be devoid, of cyclic silicone oil.

The $C_7$-$C_{14}$ volatile linear alkane(s) present in the composition make(s) it possible to obtain a water-in-oil emulsion which can be worked for a long time during application, despite a content of pulverulent materials (for example: pigments, fillers) of greater than 10%, or even greater than 20%, by weight, relative to the total weight of said composition.

The $C_7$-$C_{14}$ volatile linear alkane(s) present in the composition also make(s) it possible, surprisingly, to fluidify the composition containing the emulsifying silicone elastomer, even with a very high level of aqueous phase.

The composition according to the invention also comprises at least one emulsifying silicone elastomer.

Silicone Elastomers

Emulsifying Silicone Elastomers

While not bound by theory, it is believed that the emulsifying silicone elastomer makes it possible to obtain a water-in-oil emulsion according to the invention with good stability. Its combination with the volatile linear alkane is believed to make it possible to obtain a texture which is both very fluid and very comfortable on application. It is also believed to provide a very soft and matting feel after application. It is also believed to improve the application properties of the composition according to the invention.

The term "emulsifying silicone elastomer" is intended to mean a silicone elastomer comprising at least one hydrophilic chain.

The emulsifying silicone elastomer may be chosen from polyoxyalkylenated silicone elastomers and polyglycerolated silicone elastomers, and mixtures thereof.

Polyoxyalkylenated Silicone Elastomers

The polyoxyalkylenated silicone elastomer is a crosslinked organopolysiloxane that can be obtained by crosslinking addition reaction of diorganopolysiloxane containing at least one hydrogen bonded to silicon and of a polyoxyalkylene having at least two ethylenically unsaturated groups.

Preferably, the polyoxyalkylenated crosslinked organopolysiloxane is obtained by crosslinking addition reaction (A1) of diorganopolysiloxane containing at least two hydrogens each bonded to a silicon, and (B1) of polyoxyalkylene containing at least two ethylenically unsaturated groups, in particular in the presence (C1) of a platinum catalyst, as described, for example, in U.S. Pat. No. 5,236,986 and U.S. Pat. No. 5,412,004.

In particular, the organopolysiloxane can be obtained by reaction of polyoxyalkylene (in particular polyoxyethylene and/or polyoxypropylene) containing dimethylvinylsiloxy end groups and of methylhydrogeno-polysiloxane containing trimethylsiloxy end groups, in the presence of a platinum catalyst.

The organic groups bonded to silicon atoms of the compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenyl-ethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes containing trimethylsiloxy end groups, copolymers of dimethylsiloxane-methylhydrogenosiloxane containing trimethylsiloxy end groups, cyclic dimethylsiloxane-methylhydrogenosiloxane copolymers, and copolymers of dimethylsiloxane-methylhydrogenosiloxane-laurylmethylsiloxane containing trimethylsiloxy end groups.

Compound (C1) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated silicone elastomers may be formed from divinyl compounds, in particular polyoxyalkylenes having at least two vinyl groups, reacting with Si—H bonds of a polysiloxane.

The polyoxyalkylenated silicone elastomer according to the invention is preferably mixed with at least one hydrocarbon-based oil and/or one silicone oil so as to form a gel. In these gels, the polyoxyalkylenated elastomer can be in the form of non-spherical particles.

Polyoxyalkylenated elastomers are in particular described in U.S. Pat. No. 5,236,986, U.S. Pat. No. 5,412,004, U.S. Pat. No. 5,837,793 and U.S. Pat. No. 5,811,487.

Polyoxyalkylenated silicone elastomers that may be used include those sold under the names KSG-21, KSG-20, KSG-30, KSG-31, KSG-32, KSG-33, KSG-210, KSG-310, KSG-320, KSG-330, KSG-340 and X-226146 by the company Shin-Etsu, and DC9010 and DC9011 by the company Dow Corning.

According to one preferred embodiment, the polyoxyalkylenated silicone elastomer sold under the name KSG-210 by the company Shin-Etsu will be used.

The emulsifying silicone elastomer may also be chosen from polyglycerolated silicone elastomers.

Polyglycerolated Silicone Elastomers

The polyglycerolated silicone elastomer is a crosslinked elastomeric organopolysiloxane that can be obtained by a crosslinking addition reaction of diorganopolysiloxane containing at least one hydrogen bonded to silicon and of polyglycerolated compounds having ethylenically unsaturated groups, in particular in the presence of a platinum catalyst.

Preferably, the crosslinked elastomeric organopolysiloxane is obtained by crosslinking addition reaction (A) of diorganopolysiloxane containing at least two hydrogens each bonded to a silicon, and (B) of glycerolated compounds having at least two ethylenically unsaturated groups, in particular in the presence (C) of a platinum catalyst.

In particular, the organopolysiloxane can be obtained by reaction of a polyglycerolated compound containing dimethylvinylsiloxy end groups and of methylhydrogenopolysiloxane containing trimethylsiloxy end groups, in the presence of a platinum catalyst.

Compound (A) is the base reactant for the formation of elastomeric organopolysiloxane and the crosslinking is performed by an addition reaction of compound (A) with compound (B) in the presence of the catalyst (C).

Compound (A) is in particular an organopolysiloxane containing at least 2 hydrogen atoms bonded to different silicon atoms in each molecule.

Compound (A) may have any molecular structure, in particular a linear chain or branched chain structure or a cyclic structure.

Compound (A) may have a viscosity at 25° C. ranging from 1 to 50 000 centistokes, in particular so as to have good miscibility with compound (B).

The organic groups bonded to the silicon atoms of compound (A) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. Preferably, said organic group is chosen from methyl, phenyl and lauryl groups.

Compound (A) can thus be chosen from methylhydrogenopolysiloxanes containing trimethylsiloxy end groups, copolymers of dimethylsiloxane-methyl-hydrogenosiloxane containing trimethylsiloxy end groups, dimethylsiloxane-methylhydrogenosiloxane cyclic copolymers, and copolymers of dimethylsiloxane-methyl-hydrogenosiloxane-laurylmethylsiloxane containing trimethylsiloxy end groups.

Compound (B) may be a polyglycerolated compound corresponding to formula (B') below:

$$C_mH_{2m-1}—O-[Gly]n-C_mH_{2m-1} \qquad (B')$$

in which m is an integer ranging from 2 to 6, n is an integer ranging from 2 to 200, preferably ranging from 2 to 100, preferably ranging from 2 to 50, preferably n ranging from 2 to 20, preferably from 2 to 10, and preferentially ranging from 2 to 5, and in particular equal to 3; Gly denotes:

—CH$_2$—CH(OH)—CH$_2$—O—  or —CH$_2$—CH (CH$_2$OH)—O— 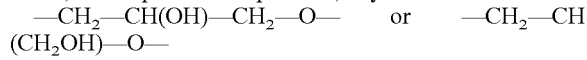

Advantageously, the sum of the number of ethylenic groups per molecule of compound (B) and of the number of hydrogen atoms bonded to silicon atoms per molecule of compound (A) is at least 4.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range of from 1/1 to 20/1.

Compound (C) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black, or platinum on a support.

The catalyst (C) is preferably added at from 0.1 to 1000 parts by weight, better still from 1 to 100 parts by weight, as clean platinum metal per 1000 parts by weight of the total amount of compounds (A) and (B).

The polyglycerolated silicone elastomer according to the invention is generally mixed with at least one hydrocarbon-based oil and/or one silicone oil so as to form a gel. In these gels, the polyglycerolated elastomer is often in the form of non-spherical particles.

Such elastomers are in particular described in patent application WO 2004/024798.

As polyglycerolated silicone elastomers, mention may be made of those sold under the names KSG-710, KSG-810, KSG-820, KSG-830 and KSG-840 by the company Shin-Etsu.

The emulsifying silicone elastomer(s) is (are) preferably present in the composition of the invention in a content ranging from 0.1% to 20%, in particular from 0.2% to 10%, and preferably from 0.5% to 5%, by weight, relative to the total weight of said composition.

In addition to the emulsifying elastomers, the composition according to the invention may comprise non-emulsifying elastomers.

Additional Non-Emulsifying Elastomers

The term "non-emulsifying" silicone elastomers defines organopolysiloxane elastomers not containing a hydrophilic chain, such as polyoxyalkylene or polyglycerolated chains.

The non-emulsifying silicone elastomer is an elastomeric crosslinked organopolysiloxane that can be obtained by a crosslinking addition reaction of diorganopolysiloxane containing at least one hydrogen bonded to silicon and of diorganopolysiloxane containing ethylenically unsaturated groups bonded to silicon, in particular in the presence of a platinum catalyst; or by a dehydrogenation crosslinking condensation reaction between a diorganopolysiloxane containing hydroxyl end groups and a diorganopolysiloxane containing at least one hydrogen bonded to silicon, in particular in the presence of an organotin; or by a crosslinking condensation reaction of a diorganopolysiloxane containing hydroxyl end groups and of a hydrolysable organopolysilane; or by thermal crosslinking of organopolysiloxane, in particular in the presence of an organoperoxide catalyst; or by crosslinking of organopolysiloxane via high-energy radiation such as gamma rays, ultraviolet rays or an electron beam.

Preferably, the elastomeric crosslinked organopolysiloxane is obtained by crosslinking addition reaction (A2) of diorganopolysiloxane containing at least two hydrogens each bonded to a silicon, and (B2) of diorganopolysiloxane containing at least two ethylenically unsaturated groups bonded to silicon, in particular in the presence (C2) of a platinum catalyst, as described, for example, in patent application EP-A-295886.

In particular, the organopolysiloxane can be obtained by reaction of dimethylpolysiloxane containing dimethylvinyl-siloxy end groups and of methylhydrogenopolysiloxane containing trimethylsiloxy end groups, in the presence of a platinum catalyst.

Compound (A2) is the base reactant for the formation of elastomeric organopolysiloxane, and the crosslinking is performed by an addition reaction of compound (A2) with compound (B2) in the presence of the catalyst (C2).

Compound (A2) is advantageously a diorganopolysiloxane containing at least two lower (for example $C_2$-$C_4$) alkenyl groups; the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (A2) may have a branched-chain, linear-chain, cyclic or networked structure, but the linear-chain structure is preferred. Compound (A2) may have a viscosity ranging from the liquid state to the gum state. Preferably, compound (A2) has a viscosity of at least 100 centistokes at 25° C.

The organopolysiloxanes (A2) may be chosen from methylvinylsiloxanes, methylvinylsiloxane-dimethyl-siloxane copolymers, dimethylpolysiloxanes containing dimethylvinylsiloxy end groups, copolymers of dimethyl-siloxane-methylphenylsiloxane containing dimethylvinyl-siloxy end groups, copolymers of dimethylsiloxane-diphenylsiloxane-methylvinylsiloxane containing dimethylvinylsiloxy end groups, copolymers of dimethyl-siloxane-methylvinylsiloxane containing trimethylsiloxy end groups, copolymers of dimethylsiloxane-methyl-phenylsiloxane-methylvinylsiloxane containing trimethylsiloxy end groups, methyl(3,3,3-tri-fluoro-propyl)polysiloxanes containing dimethylvinylsiloxy end groups, and copolymers of dimethylsiloxane-methyl-(3,3,3-trifluoropropyl)siloxane containing dimethylvinylsiloxy end groups.

Compound (B2) is in particular an organopolysiloxane containing at least 2 hydrogens bonded to silicon in each molecule and is thus the crosslinking agent for compound (A2).

Advantageously, the sum of the number of ethylenic groups per molecule of compound (A2) and the number of hydrogen atoms bonded to silicon per molecule of compound (B2) is at least 4.

Compound (B2) may be in any molecular structure, in particular of linear-chain or branched-chain structure, or cyclic structure.

Compound (B2) may have a viscosity at 25° C. ranging from 1 to 50 000 centistokes, in particular so as to have good miscibility with compound (A).

It is advantageous for compound (B2) to be added in an amount such that the molecular ratio between the total amount of hydrogen atoms bonded to silicon in compound (B2) and the total amount of all the ethylenically unsaturated groups in compound (A2) is within the range of from 1/1 to 20/1.

Compound (B2) may be chosen from methylhydrogeno-polysiloxanes containing trimethylsiloxy end groups, copolymers of dimethylsiloxane-methylhydrogenosiloxane containing trimethylsiloxy end groups, and dimethyl-siloxane-methylhydrogenosiloxane cyclic copolymers.

Compound (C2) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black, or platinum on a support.

The catalyst (C2) is preferably added at from 0.1 to 1000 parts by weight, better still from 1 to 100 parts by weight, as clean platinum metal per 1000 parts by weight of the total amount of compounds (A2) and (B2).

Other organic groups may be bonded to silicon in the organopolysiloxanes (A2) and (B2) described above, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The non-emulsifying silicone elastomer according to the invention can be mixed with at least one hydrocarbon-based oil and/or one silicone oil so as to form a gel. In these gels, the non-emulsifying elastomer is in the form of non-spherical particles.

Non-emulsifying elastomers that may be used include those sold under the names KSG-6, KSG-15, KSG-16, KSG- 18, KSG-41, KSG-42, KSG-43, KSG-44, USG-105 and USG-106 by the company Shin-Etsu, DC9040, DC9041, DC9509, DC9505, DC9506, DC5930, DC9350, DC9045 and DC9043 by the company Dow Corning, Gransil by the company Grant Industries, and SFE 839 by the company General Electric.

According to one particular embodiment, the non-emulsifying elastomer sold under the name KSG-16 by the company Shin-Etsu is used.

The non-emulsifying elastomer(s) may be present in a content ranging from 0.1% to 20% by weight, relative to the total weight of the composition, preferably ranging from 0.2% to 10% by weight, and more preferentially ranging from 0.5% to 5% by weight.

According to one particular embodiment of the invention, the composition comprises at least one polyoxyalkylenated silicone elastomer.

According to one particular embodiment, the composition comprises at least one polyoxyalkylenated silicone elastomer and at least one non-emulsifying silicone elastomer.

According to one particular embodiment of the invention, the composition also comprises at least 10% by weight of pulverulent materials, relative to the total weight of said composition.

Pulverulent Materials

The term "pulverulent materials" is intended to mean any particles of dyestuff and/or filler type, as defined hereinafter.

In particular, the composition comprises at least one pulverulent material chosen from pigments, pearlescent agents and fillers, and mixtures thereof, in particular pigments.

The pulverulent materials are preferably present in the composition in a content ranging from 10% to 50% by weight, in particular from 15% to 40% by weight, and especially from 20% to 30% by weight, relative to the total weight of said composition.

Said pulverulent materials are dispersed in a homogeneous and stabilized form.

According to one embodiment, the composition of the invention comprises at least one filler.

Fillers

A composition in accordance with the invention may also comprise at least one filler of organic or inorganic nature.

The term "filler" should be understood to mean colourless or white solid particles of any shape which are in a form that is insoluble and dispersed in the medium of the composition. They are inorganic or organic in nature and make it possible to confer softness and mattness on the composition and a uniform makeup result.

The fillers may be present in the emulsion in a content ranging from, for example, 0.5% to 20% by weight, relative to the total weight of the emulsion, preferably 2% to 10%.

The fillers used in the compositions according to the present invention may be in lamellar, globular or spherical form, in the form of fibres or in any other intermediate form between these defined forms.

The fillers according to the invention may be uncoated or surface-coated, and in particular they may be surface-treated with silicones, amino acids, fluoro derivatives or any other substance that promotes the dispersion and compatibility of the filler in the composition.

Among the inorganic fillers that can be used in the compositions according to the invention, mention may be made of talc, mica, silica, trimethyl siloxysilicate, kaolin, bentone, calcium carbonate and magnesium hydrogen carbonate, hydroxyapatite, boron nitride, hollow silica microspheres (silica beads from Maprecos), glass or ceramic microcapsules, silica-based fillers such as Aerosil 200 or Aerosil 300; Sunsphere H-33 and Sunsphere H-51 sold by Asahi Glass; Chemicelen sold by Asahi Chemical; composites of silica and of titanium dioxide, such as the TSG series sold by Nippon Sheet Glass, and mixtures thereof.

Among the organic fillers that can be used in the compositions according to the invention mention may be made of polyamide powders (Nylon® Orgasol from Atochem), poly-β-alanine and polyethylene powders, polytetra-fluoroethylene (Teflon®) powders, lauroyllysine, starch, tetrafluoroethylene polymer powders, hollow polymer microspheres, such as Expancel (Nobel Industrie), metal soaps derived from organic carboxylic acids containing from 8 to 22 carbon atoms, preferably from 12 to 18 carbon atoms, for example zinc stearate, magnesium stearate or lithium stearate, zinc laurate, magnesium myristate, Polypore® L 200 (Chemdal Corporation), silicone resin microbeads (Tospearl® from Toshiba, for example), polyurethane powders, in particular powders of crosslinked polyurethane comprising a copolymer, said copolymer comprising trimethylol hexyllactone, for instance the hexa-methylene diisocyanate/trimethylol hexyllactone polymer sold under the name Plastic Powder D-400® or Plastic Powder D-800® by the company Toshiki, carnauba microwaxes, such as the products sold under the name Micro-Care 350® by the company Micro Powders, microwaxes of synthetic wax, such as the products sold under the name MicroEase 114S® by the company Micro Powders, microwaxes constituted of a mixture of carnauba wax and of polyethylene wax, such as those sold under the names MicroCare 300® and 310® by the company Micro Powders, microwaxes constituted of a mixture of carnauba wax and of synthetic wax, such as the product sold under the name MicroCare 325® by the company Micro Powders, polyethylene microwaxes, such as those sold under the names Micropoly 200®, 220®, 220L® and 250S® by the company Micro Powders; fibres of synthetic or natural and inorganic or organic origin. They may be short or long, individual or organised, for example twisted, and hollow or solid. They can have any shape and can in particular be circular or polygonal (square, hexagonal or octagonal) in cross section, according to the specific application envisaged. In particular, their ends are blunted and/or polished to prevent injury. The fibres have a length ranging from 1 µm to 10 mm, preferably from 0.1 mm to 5 mm, and better still from 0.3 mm to 3 mm. Their cross section can be included within a circle having a diameter ranging from 2 nm to 500 µm, preferably ranging from 100 nm to 100 µm, and better still from 1 µm to 50 µm. As fibres that can be used in the compositions according to the invention, mention may be made of non-rigid fibres such as polyamide (Nylon®) fibres or rigid fibres such as polyimide-amide fibres, for instance those sold under the names Kermel® and Kermel Tech® by the company Rhodia, or poly(p-phenyleneterephthalamide) (or aramid) fibres, sold in particular under the name Kevlar® by the company Du Pont de Nemours;
and mixtures thereof.

According to one embodiment, the composition of the invention comprises at least one pulverulent dyestuff, in particular at least one pigment.

Pulverulent Dyestuffs

The pulverulent dyestuffs may be present in a proportion, for example, of from 3% to 30% by weight, especially from 8% to 20% by weight, and in particular from 10% to 15% by weight, relative to the total weight of the cosmetic composition.

The pulverulent dyestuffs are in particular chosen from organic or inorganic pulverulent dyestuffs, in particular of pigment or pearlescent agent type, materials with a specific optical effect, and mixtures thereof.

According to one particular embodiment, the pulverulent dyestuffs are surface-treated with a hydrophobic agent. The hydrophobic treatment agent can be chosen from silicones, for instance methicones, dimethicones or perfluoroalkylsilanes; fatty acids, for instance stearic acid; metal soaps, for instance aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, and amino acids; N-acylamino acids or salts thereof; lecithin, isopropyl triisostearyl titanate, and mixtures thereof.

Pigments

The term "pigments" should be understood to mean white or coloured, mineral or organic particles which are insoluble in an aqueous solution, and which are intended to colour and/or opacify the resulting film.

As mineral pigments that can be used in the invention, mention may be made of titanium oxides, zirconium oxides or cerium oxides, and also zinc oxides, iron oxides or chromium oxides, ferric blue, manganese violet, ultramarine blue and chromium hydrate.

Iron oxide or titanium dioxide pigments are preferably used.

The pigment may be a pigment having a structure which may be, for example, of sericite/brown iron oxide/titanium dioxide/silica type. Such a pigment is sold, for example, under the reference Coverleaf NS or JS by the company Chemicals and Catalysts and has a contrast ratio in the region of 30.

The dyestuff may also comprise a pigment having a structure which may be, for example, of the type such as silica microspheres containing iron oxide. An example of a pigment having this structure is the product sold by the company Miyoshi under the reference PC Ball PC-LL-100 P, this pigment being constituted of silica microspheres containing yellow iron oxide.

Among the organic pigments that can be used in the invention, mention may be made of carbon black, D & C pigments, lakes based on cochineal carmine, on barium, strontium, calcium or aluminium, or else the diketopyrrolopyrroles (DPPs) described in documents EP-A-542669, EP-A-787730, EP-A-787731 and WO-A-96/08537.

Other pigments that can also be used include composite pigments as described in application EP 1 545 437. These composite pigments may be composed in particular of particles comprising an inorganic core coated at least partially with an organic pigment and at least one binder which binds the organic pigments to the core.

The inorganic core may be made of a material chosen from the nonlimiting list comprising metal salts and metal oxides, in particular titanium oxide, zirconium oxide, cerium oxide, zinc oxide, iron oxide, ferric blue oxide, aluminium oxide and chromium oxide, aluminas, glasses, ceramics, graphite, silicas, silicates, in particular aluminosilicates and borosilicates, synthetic mica, and mixtures thereof. According to one particular embodiment, the inorganic core is a titanium oxide.

The organic dyestuff may comprise, for example, organic pigments which can be chosen from the compounds below and mixtures thereof:

cochineal carmine, organic pigments of azo, anthraquinone, indigoid, xanthene, pyrene, quinoline, triphenylmethane or fluorane dyes, insoluble organic sodium, potassium, calcium, barium, aluminium, zirconium, strontium or titanium salts or organic lakes of acid dyes such as azo, anthraquinone, indigoid, xanthene, pyrene, quinoline, triphenylmethane or fluorane dyes, it being possible for these dyes to comprise at least one carboxylic or sulphonic acid group.

According to one particular embodiment, the D&C Red No. 7 organic pigment is used.

According to another embodiment, the D&C Red No. 28 organic pigment is used.

As examples of composite pigments that can be used according to the invention, alone or as a mixture, mention may in particular be made of:

titanium dioxide (CI77891), FD&C Blue Aluminium lake (CI42090) and polymethylhydrogensiloxane (58.1/40.7/1.2), titanium dioxide (CI77891), D&C Red No. 7 (CI15850) and polymethylhydrogensiloxane (65.8/32.9/1.3), titanium dioxide (CI77891), D&C Red No. 28 (CI45410) and polymethylhydrogensiloxane (65.8/32.9/1.3), titanium dioxide (CI77891), FD&C Yellow 5 Aluminium lake (CI191140) and polymethylhydrogensiloxane (65.8/32.9/1.3).

Advantageously, the pigments can be present in a hydrophobic coated form in the emulsion according to the invention. They are more particularly pigments that have been surface-treated with a hydrophobic agent in order to render them compatible with the fatty phase of the emulsion, in particular in order for them to have good wettability with the oils of the fatty phase. Thus, the treated pigments are well dispersed in the fatty phase.

The hydrophobic treatment agent can be chosen from silicones, such as methicones, dimethicones or perfluoroalkylsilanes; fatty acids, such as stearic acid; metal soaps, such as aluminium dimyristate or the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, amino acids; N-acylamino acids or salts thereof; lecithin, isopropyl triisostearyl titanate, and mixtures thereof.

The N-acylamino acids can comprise an acyl group containing from 8 to 22 carbon atoms, for instance a 2-ethylhexanoyl, caproyl, lauroyl, myristoyl, palmitoyl, stearoyl or cocoyl group. The salts of these compounds can be aluminium, magnesium, calcium, zirconium, zinc, sodium or potassium salts. The amino acid can, for example, be lysine, glutamic acid or alanine.

The term "alkyl" mentioned in the above-mentioned compounds denotes in particular an alkyl group containing from 1 to 30 carbon atoms, preferably containing from 5 to 16 carbon atoms.

Hydrophobically treated pigments are in particular described in application EP-A-1086683.

Pearlescent Agents

The term "pearlescent agents" should be understood to mean coloured particles of any shape, which may or may not be iridescent, produced in particular by certain shellfish in their shells or else synthesized, which exhibit a colour effect by optical interference.

The pearlescent agents can be chosen from pearlescent pigments, such as titanium mica coated with an iron oxide, titanium mica coated with bismuth oxychloride, titanium mica coated with chromium oxide, titanium mica coated with an organic dye, and also pearlescent pigments based on bismuth oxychloride. They may also be mica particles at the surface of which at least two successive layers of metal oxides and/or of organic dyestuffs are superposed.

By way of example of pearlescent agents, mention may also be made of natural mica coated with titanium oxide, with iron oxide, with natural pigment or with bismuth oxychloride.

Materials with an Optical Effect

The cosmetic composition according to the invention may also contain at least one material with a specific optical effect.

This effect is different from a simple conventional colouring effect, i.e. a unified and stabilized effect, such as that produced by conventional dyestuffs, for instance monochromatic pigments. For the purpose of the invention, the term "stabilized" means devoid of an effect of variability of the colour with the angle of observation or else in response to a change in temperature.

For example, this material can be chosen from particles with a metallic glint, goniochromatic colouring agents, diffracting pigments, thermochromic agents, optical brighteners, and also fibres, in particular interference fibres. Of course, these various materials can be combined so as to provide the simultaneous display of two effects, or even of a novel effect in accordance with the invention.

The particles with a metallic glint which can be used in the invention are in particular chosen from:
- particles of at least one metal and/or of at least one metal derivative,
- particles comprising an organic or inorganic substrate, made of one material or many materials, at least partially coated with at least one layer with a metallic glint comprising at least one metal and/or at least one metal derivative, and
- mixtures of said particles.

Among the metals that may be present in said particles, mention may, for example, be made of Ag, Au, Cu, Al, Ni, Sn, Mg, Cr, Mo, Ti, Zr, Pt, Va, Rb, W, Zn, Ge, Te, Se and mixtures or alloys thereof. Ag, Au, Cu, Al, Zn, Ni, Mo, Cr, and mixtures or alloys thereof (for example, bronzes and brasses) are preferred metals.

The term "metal derivatives" denotes compounds derived from metals, in particular oxides, fluorides, chlorides and sulphides.

The goniochromatic colouring agent can be chosen, for example, from interference multilayer structures and liquid crystal colouring agents.

Galenics

In addition to the compounds described above, the water-in-oil emulsion according to the invention comprises an aqueous phase dispersed in a liquid fatty phase, and comprises at least one physiologically acceptable medium.

According to one particular embodiment of the invention, the composition of the invention has an aqueous phase to liquid fatty phase ratio of greater than 1, preferably greater than 1.5, preferably greater than 2.

The term "physiologically acceptable medium" is intended to denote a medium that is particularly suitable for the application of a composition of the invention to keratin materials, in particular the skin and the lips.

The physiologically acceptable medium is generally adapted to the nature of the substrate onto which the composition is to be applied, and also to the way in which the composition is to be packaged.

Aqueous Phase

A composition according to the invention comprises at least one aqueous phase, preferably in a content ranging from 10% to 80%, preferably from 30% to 70%, more preferentially between 40% and 60% by weight, relative to the total weight of the composition.

The aqueous phase comprises water and/or at least one water-soluble solvent.

The water may be a floral water such as cornflower water and/or a mineral water such as Vittel water, Lucas water or La Roche Posay water and/or a spring water.

The term "water-soluble solvent" denotes, in the present invention, a compound that is liquid at ambient temperature and water-miscible (water-miscibility greater than 50% by weight at 25° C. and atmospheric pressure).

The water-soluble solvent(s) suitable for the invention may be chosen from $C_{1-8}$, and in particular $C_{1-5}$, monoalcohols, in particular ethanol, isopropanol, tert-butanol or n-butanol, polyols as described previously, and mixtures thereof. Also most particularly suitable for the invention are ethanol and isopropanol, and preferably ethanol.

A composition of the invention may also comprise at least one salt, for example sodium chloride, magnesium chloride and magnesium sulphate.

A composition of the invention may comprise from 0.05% to 1.5%, in particular from 0.1% to 10%, and more particularly from 0.15% to 0.8% by weight of salts, relative to the total weight of the composition.

The aqueous phase may also comprise any water-soluble or water-dispersible compound that is compatible with an aqueous phase, such as gelling agents, film-forming polymers, thickeners, surfactants, and mixtures thereof.

Liquid Fatty Phase

A cosmetic composition in accordance with the present invention comprises at least one liquid fatty phase comprising at least one or more volatile linear alkanes as defined above and, optionally, at least one additional oil.

A composition of the invention may comprise a liquid fatty phase in a content ranging for example from 10% to 80%, in particular from 15% to 60%, and more particularly from 15% to 40% by weight, relative to the total weight of the composition.

According to one particular embodiment of the invention, the composition of the invention will have an aqueous phase to liquid fatty phase ratio of greater than 1, preferably greater than 1.5, preferably greater than 2.

A compositing according to the invention may comprise at least one additional oil, chosen from volatile and non-volatile oils of hydrocarbon-based, silicone or fluoro type. The oils may be of animal, plant, mineral or synthetic origin.

The term "oil" is intended to mean any fatty substance that is in liquid form at ambient temperature (20-25° C.) and at atmospheric pressure.

The term "volatile oil" is intended to mean an oil (or non-aqueous medium) capable of evaporating on contact with the skin in less than one hour at ambient temperature and atmospheric pressure. The volatile oil is a volatile cosmetic oil, which is liquid at ambient temperature, having in particular a non-zero vapour pressure, at ambient temperature and atmospheric pressure, in particular having a vapour pressure ranging from 0.13 Pa to 40 000 Pa ($10^{-3}$ to 300 mmHg), and preferably ranging from 1.3 Pa to 13 000 Pa (0.01 to 100 mmHg), and preferentially ranging from 1.3 Pa to 1300 Pa (0.01 to 10 mmHg).

In addition, the volatile oil generally has a boiling point, measured at atmospheric pressure, ranging from 150° C. to 260° C., and preferably ranging from 170° C. to 250° C.

Advantageously, the fatty phase comprises from 5% to 40% by weight, preferably from 7% to 30% by weight, and preferentially from 10% to 20% by weight of volatile oil(s), relative to the total weight of the composition.

The term "hydrocarbon-based oil" is intended to mean an oil formed essentially of, or even constituted of, carbon and hydrogen atoms and, optionally, oxygen and nitrogen atoms, and not containing a silicon or fluorine atom; it can contain ester, ether, amine and amide groups.

The term "silicone oil" is intended to mean an oil containing at least one silicon atom, and in particular containing Si—O groups.

The term "fluoro oil" is intended to mean an oil containing at least one fluorine atom.

Additional Volatile Oils

The volatile hydrocarbon-based oil that can be used in the invention can be chosen from hydrocarbon-based oils having a flashpoint ranging from 40° C. to 102° C., preferably ranging from 40° C. to 55° C., and preferentially ranging from 40° C. to 50° C.

As volatile hydrocarbon-based oils, mention may be made of volatile hydrocarbon-based oils containing from 8 to 16 carbon atoms and mixtures thereof, and in particular branched $C_8$-$C_{16}$ alkanes, such as $C_8$-$C_{16}$ isoalkanes (also known as isoparaffins), isododecane, isodecane, isohexadecane and, for example, the oils sold under the trade names Isopar or Permethyl, branched $C_8$-$C_{16}$ esters, such as isohexyl neopentanoate, and mixtures thereof. Preferably, the volatile hydrocarbon-based oil is chosen from volatile hydrocarbon-based oils containing from 8 to 16 carbon atoms and mixtures thereof, in particular from isododecane, isodecane and isohexadecane, and is in particular isododecane.

The volatile silicone oil that can be used in the invention can be chosen from silicone oils having a flashpoint ranging from 40° C. to 102° C., preferably having a flashpoint of greater than 55° C. and less than or equal to 95° C., and preferentially ranging from 65° C. to 95° C.

As volatile silicone oils, mention may be made of linear or cyclic silicone oils having from 2 to 7 silicon atoms, these silicones optionally comprising alkyl or alkoxy groups containing from 1 to 10 carbon atoms. As examples of a volatile silicone oil, mention may in particular be made of octamethylcyclotetra-siloxane, decamethylcyclopentasiloxane, dodecamethyl-cyclohexasiloxane, heptamethylhexyltrisiloxane, hepta-methyloctyltrisiloxane, hexamethyldisiloxane, octa-methyltrisiloxane, decamethyltetrasiloxane, dodecamethylpentasiloxane, and mixtures thereof.

As volatile fluoro oils, mention may be made of nonafluoroethoxybutane, nonafluoromethoxybutane, deca-fluoropentane, tetradecafluorohexane, dodecafluoro-pentane, and mixtures thereof.

The additional volatile oil may be present in a content ranging from 5% to 30% by weight, relative to the total weight of the emulsion, preferably ranging from 8% to 20% by weight, and preferentially ranging from 10% to 15% by weight, relative to the total weight of the composition. The fatty phase of the emulsion according to the invention may also comprise at least one non-volatile oil.

Non-Volatile Oils

This non-volatile oil or a mixtures thereof may be present in a content ranging for example from 1% to 30% by weight, relative to the total weight of the emulsion, and preferably ranging from 2% to 20% by weight.

The non-volatile oil may be chosen from carbon-based, hydrocarbon-based and/or silicone oils of mineral, animal, plant or synthetic origin, and mixtures thereof, in so far as they are compatible with the use envisaged.

Mention may be made of non-volatile hydrocarbon-based oils such as liquid paraffin or liquid petroleum jelly, isoeicosane, soybean oil, perhydrosqualene, sweet almond oil, calophyllum oil, palm oil, grapeseed oil, sesame oil, maize oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, di(2-ethylhexyl)succinate, diisostearyl malate, glyceryl triisostearate or diglyceryl triisostearate; higher fatty acids, such as myristic acid, palmitic acid, stearic acid, behenic acid, oleic acid, linoleic acid, linolenic acid or isostearic acid; higher fatty alcohols, such as cetanol, stearyl alcohol or oleyl alcohol, linoleyl or linolenyl alcohol, isostearyl alcohol or octyldodecanol.

As non-volatile silicone oils, mention may be made of polydimethylsiloxanes (PDMSs), which are optionally phenylated, such as phenyl trimethicones, or optionally substituted with aliphatic and/or aromatic groups or with functional groups, such as hydroxyl, thiol and/or amine groups; polysiloxanes modified with fatty acids, fatty alcohols or polyoxyalkylenes, and mixtures thereof.

According to one particular embodiment, isononyl isononanoate will be used.

Additional Surfactants

A composition according to the invention comprises an emulsifying silicone elastomer and, optionally, one or more additional surfactant(s) suitable for W/O emulsions, in particular chosen from amphoteric, anionic, cationic or nonionic surfactants, used alone or as mixtures.

The surfactants are generally present in the composition in a content that can range for example from 0.5% to 15% by weight, in particular from 1.0% to 5% by weight, relative to the total weight of the composition.

By way of example, the silicone surfactant(s) may be present in a content ranging from 0.5% to 10% by weight, in particular from 1% to 5% by weight, relative to the total weight of the composition.

According to another particular embodiment, the non-silicone surfactant(s) may be present in a content ranging from 0.1% to 10% by weight, in particular from 0.5% to 8% by weight, relative to the total weight of the composition.

For the W/O emulsions, hydrocarbon-based or silicone surfactants may in particular be used.

As hydrocarbon-based surfactants, mention may be made, for example, of polyesters of polyols, such as PEG-30 dipolyhydroxystearate, sold under the reference Arlacel P 135 by the company Uniqema, and polyglyceryl-2 dipolyhydroxystearate sold under the reference Dehymuls PGPH by Cognis.

As silicone surfactants, mention may, for example, be made of alkyl dimethicone copolyols, such as the lauryl methicone copolyol sold under the name "Dow Corning 5200 Formulation Aid" by the company Dow Corning, and the cetyl dimethicone copolyol sold under the name Abil EM 90 by the company Goldschmidt, or the polyglyceryl-4 isostearate/cetyl dimethicone copolyol/hexyl laurate mixture sold under the name Abil WE 09 by the company Goldschmidt.

One or more coemulsifiers may also be added thereto. Advantageously, the coemulsifier may be chosen from the group comprising polyol alkyl esters. As polyol alkyl esters, mention may in particular be made of esters of glycerol and/or of sorbitan, for example the polyglyceryl-3 diisostearate sold under the name Lameform TGI by the company Cognis, polyglyceryl-4 isostearate, such as the product sold under the name Isolan GI 34 by the company Goldschmidt, sorbitan isostearate, such as the product sold under the name Arlacel 987 by the company ICI, glycerol sorbitan isostearate, such as the product sold under the name Arlacel 986 by the company ICI, and mixtures thereof.

According to one particularly preferred embodiment, an emulsion according to the invention, in particular a W/O emulsion comprising a silicone oily phase, comprises at least one silicone surfactant more particularly chosen from dimethicone copolyols.

The presence of a dimethicone copolyol promotes in particular the stabilization of the emulsion according to the invention.

A dimethicone copolyol that can be used according to the invention is an oxypropylenated and/or oxyethylenated polydimethylmethylsiloxane.

As dimethicone copolyol, use may be made of those corresponding to the following formula (II):

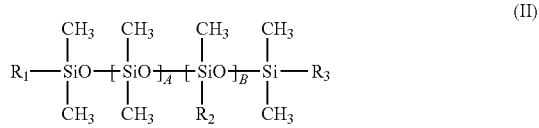

in which:

$R_1$, $R_2$ and $R_3$, independently of one another, represent a $C_1$-$C_6$ alkyl radical or a —$(CH_2)_x$—$(OCH_2CH_2)_y$—$(OCH_2CH_2)_z$—$OR_4$ radical, at least one $R_1$, $R_2$ or $R_3$ radical not being an alkyl radical; $R_4$ being a hydrogen, a $C_1$-$C_3$ alkyl radical or a $C_2$-$C_4$ acyl radical;

A is an integer ranging from 0 to 200;

B is an integer ranging from 0 to 50; provided that A and B are not equal to zero at the same time;

x is an integer ranging from 1 to 6;

y is an integer ranging from 1 to 30; and z is an integer ranging from 0 to 5.

According to one preferred embodiment of the invention, in the compound of formula (II), $R_1$=$R_3$=methyl radical, x is an integer ranging from 2 to 6, and y is an integer ranging from 4 to 30. $R_4$ is in particular a hydrogen.

By way of examples of compounds of formula (II), mention may be made of the compounds of formula (III):

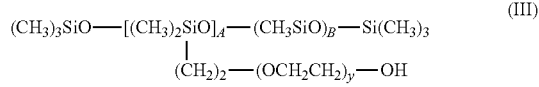

in which A is an integer ranging from 20 to 105, B is an integer ranging from 2 to 10 and y is an integer ranging from 10 to 20.

By way of examples of silicone compounds of formula (II), mention may also be made of the compounds of formula (IV):

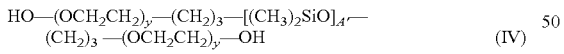

in which A' and y are integers ranging from 10 to 20.

Dimethicone copolyols that may be used also include those sold under the names DC 5329, DC 7439-146, DC 2-5695 and Q4-3667 by the company Dow Corning; and KF-6013, KF-6015, KF-6016, KF-6017 and KF-6028 by the company Shin-Etsu.

The compounds DC 5329, DC 7439-146 and DC 2-5695 are compounds of formula (III) in which, respectively, A is 22, B is 2 and y is 12; A is 103, B is 10 and y is 12; A is 27, B is 3 and y is 12.

According to one particular embodiment, the silicone surfactant may be PEG-9 polydimethylsiloxyethyl dimethicone, sold in particular by the company Shin-Etsu under the reference KF-6028, PEG-10 dimethicone, sold in particular by Shin-Etsu under the reference KF-6017, and mixtures thereof.

The dimethicone copolyol may be present in the composition according to the invention in a content ranging from 0.5% to 6% by weight, relative to the total weight of the emulsion, and preferably ranging from 1.0% to 3% by weight.

According to one particular embodiment of the invention the composition comprises, in addition to the emulsifying silicone elastomer, at least one silicone surfactant and at least one hydrocarbon-based surfactant.

Preferably, said silicone surfactant is chosen from dimethicone copolyols and said hydrocarbon-based surfactant is chosen from polyol alkyl esters.

Cosmetic Adjuvants

The compositions of the invention may also contain one or more of the adjuvants that are customary in the cosmetics and dermatological fields, such as moisturizing agents; emollients; hydrophilic or lipophilic active agents; free-radical scavengers; sequestering agents; antioxidants; preservatives; basifying or acidifying agents; fragrances; hydrophilic gelling agents; film-forming agents, in particular film-forming polymers (for compositions in a sustained direction), organic or physiological sunscreens, water-soluble or fat-soluble dyes; and mixtures thereof. The amounts of these various adjuvants are those conventionally used in foundations.

The composition of the invention may thus also comprise at least one film-forming agent in the aqueous phase and/or in the oily phase in order to reinforce the staying power of the composition.

Of course, those skilled in the art will take care to select the optional adjuvant(s) added to the composition according to the invention in such a way that the advantageous properties intrinsically attached to the composition in accordance with the invention are not, or not substantially, detrimentally affected by the envisaged addition.

These adjuvants are generally present in the composition in a content ranging from 0.01% to 20% by weight, preferably from 0.1% to 10% by weight, relative to the total weight of said composition.

According to one particular embodiment, the composition of the invention does not comprise a gelling agent and/or a structuring agent.

The invention is illustrated in the examples presented hereinafter by way of illustration and without implied limitation of the field of the invention:

Unless otherwise indicated, the values in the examples below are expressed as % by weight, relative to the total weight of the composition.

EXAMPLES

Example 1

Example of a Foundation According to the Invention and Comparative Example

| Phase | | Invention | Comparative |
|---|---|---|---|
| A1 | Emulsifying silicone elastomer (1) | 2.50 | 2.50 |
| | Dimethicone 6 cst | 6.80 | 12.80 |
| A2 | Predominant mixture of n-undecane:n-tridecane in which the n-undecane is predominant in the mixture* | 6.00 | 0.00 |
| | Isododecane | 5.00 | 5.00 |
| | Isononyl isonanoate | 5.00 | 5.00 |

-continued

| Phase | | Invention | Comparative |
|---|---|---|---|
| | Polyglyceryl diisostearate | 1.00 | 1.00 |
| | PEG-10 Dimethicone (2) | 1.50 | 1.50 |
| | Surface-treated iron oxide (3) | 3.40 | 3.40 |
| | Surface-treated titanium oxide (3) | 8.60 | 8.60 |
| | Surface-treated titanium nano-oxide (4) | 4.00 | 4.00 |
| A3 | Nylon powder | 2.00 | 2.00 |
| | Spherical silica | 2.00 | 2.00 |
| B | Water | 44.50 | 44.50 |
| | Magnesium sulphate | 0.50 | 0.50 |
| | Preservative | 1.20 | 1.20 |
| | Propylene glycol | 2.00 | 2.00 |
| | Butylene glycol | 4.00 | 4.00 |
| | TOTAL | 100.00 | 100.00 |

(1) KSG 210 from Shin-Etsu
*as prepared according to application WO 2008/155059
(2) KF6017 from Shin-Etsu
(3) NAI pigments from Miyoshi
(4) Mibrid SAS TTO-S3 pigment from Miyoshi Phase A1 is obtained by diluting the silicone elastomer in the dimethicone. The pigments are then ground in the oils of phase A2 and added to phase A1. The ingredients of aqueous phase B are mixed and phase B is then poured into phase A so as to form the emulsion.

The two formulations have an aqueous phase to liquid fatty phase ratio of 50.5/22.8.

The formulation according to the invention is very fluid, whereas the comparative example is very thick.

The foundation according to the invention slides better, can be applied more easily, and can be worked for a longer period of time than the comparative example.

Example 2

Foundation Example

| Phase | | |
|---|---|---|
| A1 | Emulsifying silicone elastomer (1) | 2.00 |
| | Silicone elastomer (2) | 0.75 |
| | Dimethicone 6 cst | 7.50 |
| A2 | Predominant mixture of n-undecane:n-tridecane in which the n-undecane is predominant in the mixture* | 5.00 |
| | Isododecane | 5.00 |
| | Isononyl isononanoate | 4.00 |
| | Polyglyceryl diisostearate | 0.75 |
| | PEG-10 Dimethicone (3) | 1.00 |
| | Surface-treated iron oxide (4) | 3.90 |
| | Surface-treated titanium oxide (4) | 10.10 |
| | Surface-treated titanium nano-oxide (5) | 3.00 |
| A3 | Nylon powder | 1.50 |
| | Spherical silica | 1.50 |
| | Sericite | 6.00 |
| B | Water | 42.00 |
| | Magnesium sulphate | 0.50 |
| | Preservative | 1.00 |
| | Propylene glycol | 1.50 |
| | Butylene glycol | 3.00 |
| | TOTAL | 100.00 |

(1) KSG 210 from Shin-Etsu
(2) KSG 16 from Shin-Etsu
*as prepared according to application WO 2008/155059
(3) KF6017 from Shin-Etsu
(4) NAI pigments from Miyoshi
(5) Mibrid SAS TTO-S3 pigment from Miyoshi Phase A1 is obtained by diluting the elastomers in the dimethicone. The pigments are then ground in the oils of phase A2 and added to phase A1. The ingredients of aqueous phase B are mixed and phase B is then poured into phase A so as to form the emulsion.

The aqueous phase to liquid fatty phase ratio of this formulation is 46.5/21.5.

The resulting foundation is fluid and stable, with a good matting effect, a very soft feel and good staying power.

Example 3

Foundation Example

| Phase | | Formula for 100 g |
|---|---|---|
| A1 | Emulsifying silicone elastomer (1) | 3.00 |
| | Dimethicone 6 cst | 6.80 |
| A2 | Predominant mixture of n-undecane:n-tridecane in which the n-undecane is predominant in the mixture* | 6.00 |
| | Isododecane | 5.00 |
| | Isononyl isononanoate | 5.00 |
| | Polyglyceryl diisostearate | 1.00 |
| | PEG-10 Dimethicone (2) | 1.50 |
| | Surface-treated iron oxide (3) | 2.30 |
| | Surface-treated titanium oxide (3) | 7.70 |
| A3 | Nylon powder | 1.00 |
| | Spherical silica | 1.00 |
| | White titanium mica pearlescent agent | 2.00 |
| B | Water | 51.00 |
| | Magnesium sulphate | 0.50 |
| | Preservative | 1.20 |
| | Propylene glycol | 2.00 |
| | Pentylene glycol | 3.00 |
| | TOTAL | 100.00 |

(1) KSG 210 from Shin-Etsu
*as prepared according to application WO 2008/155059
(2) KF6017 from Shin-Etsu
(3) NAI pigments from Miyoshi Phase A1 is obtained by diluting the elastomer in the dimethicone. The pigments are then ground in the oils of phase A2 and added to phase A1. The ingredients of aqueous phase B are mixed and phase B is then poured into phase A so as to form the emulsion.

The resulting foundation is fluid and stable, with a satin and luminous finish, a very soft feel and good staying power.

The aqueous phase to liquid fatty phase ratio of this formulation is 56/22.8.

Example 4

Foundation Example

| Phase | | Formula for 100 g |
|---|---|---|
| A1 | Emulsifying silicone elastomer (1) | 3.00 |
| | Dimethicone 6 cst | 6.80 |
| A2 | Dodecane (Parafol 12 from Sasol) | 6.00 |
| | Isododecane | 5.00 |
| | Isononyl isononanoate | 5.00 |
| | Polyglyceryl diisostearate | 1.00 |
| | PEG-10 Dimethicone (2) | 1.50 |

-continued

| Phase | | Formula for 100 g |
|---|---|---|
| | Surface-treated iron oxide (3) | 2.30 |
| | Surface-treated titanium oxide (3) | 7.70 |
| A3 | Nylon powder | 1.00 |
| | Spherical silica | 1.00 |
| | White titanium mica pearlescent agent | 2.00 |
| B | Water | 51.00 |
| | Magnesium sulphate | 0.50 |
| | Preservative | 1.20 |
| | Propylene glycol | 2.00 |
| | Pentylene glycol | 3.00 |
| | TOTAL | 100.00 |

(1) KSG 210 from Shin-Etsu
*as prepared according to application WO 2008/155059
(2) KF6017 from Shin-Etsu
(3) NAI pigments from Miyoshi The composition is prepared as indicated in Example 3.

The foundation is fluid and stable, with a very soft feel and good staying power.

The aqueous phase to liquid fatty phase ratio of this formulation is 56/22.8.

Example 5

Example of a Foundation According to the Invention and Comparative Example

| Phase | | Invention | Comparative |
|---|---|---|---|
| A1 | Emulsifying silicone elastomer (1) | 4.00 | 0.00 |
| | Cetyl PEG/PPG-10/1 dimethicone (2) | 0.00 | 1.00 |
| | Dimethicone 6 cst | 6.50 | 9.50 |
| A2 | n-undecane/n-tridecane mixture in which the n-undecane is predominant in the mixture* | 6.50 | 6.50 |
| | Isododecane | 5.00 | 5.00 |
| | Isodecyl neopentanoate | 5.00 | 5.00 |
| | Polyglyceryl diisostearate | 1.00 | 1.00 |
| | PEG-10 dimethicone (3) | 1.50 | 1.50 |
| | Surface-treated iron oxide (4) | 2.40 | 2.40 |
| | Surface-treated titanium oxide (4) | 11.60 | 11.60 |
| A3 | Boron nitride | 2.00 | 2.00 |
| B | Water | 47.00 | 47.00 |
| | Magnesium sulphate | 0.50 | 0.50 |
| | Preservative | 1.00 | 1.00 |
| | Propylene glycol | 2.00 | 2.00 |
| | Glycerol | 4.00 | 4.00 |
| | TOTAL | 100.00 | 100.00 |

(1) KSG 210 from Shin-Etsu
(2) Abil EM90 from Evonik Goldschmidt
*as prepared according to application WO 2008/155059
(3) KF6017 from Shin-Etsu
(4) NAI pigments from Miyoshi Phase A1 is obtained by diluting the silicone elastomer, when present (invention), in the dimethicone. The pigments are then ground in the oils of phase A2 and added to phase A1. The ingredients of aqueous phase B are mixed and phase B is then poured into phase A so as to form the emulsion.

Stability study: The macroscopic and microscopic appearance of the composition (quality of the emulsion) is evaluated 24 hours after the preparation of the composition, and also after 2 months of storage.

The composition according to the invention is fluid and very stable and gives a unifying makeup result. The comparative example is very fluid and the emulsion has a very poor stability: a considerable release of oil appears after a few days.

These results confirm that the use of an emulsifying silicone elastomer according to the invention (for example: KSG210) in a water-in-oil emulsion in combination with an, in particular C7-C14, volatile linear alkane makes it possible to obtain a fluid and very stable composition, compared with the use of a non-elastomeric silicone emulsifier, such as cetyl PEG/PPG-10/1 dimethicone (for example: Abil EM 90), at an equivalent active material content, in the same architecture.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more."

The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition in the form of a water-in-oil emulsion having an aqueous phase and liquid fatty phase, said composition comprising water and:
   (i) at least one volatile linear alkane, and
   (ii) at least one emulsifying silicone elastomer selected from the group consisting of a polyoxyalkylenated silicone elastomer and a polyglycerolated silicone elastomer,
   wherein the composition exhibits good stability, a fluid nature, easy application and a soft and matting final result.

2. The composition according to claim 1, further comprising at least 10% by weight of at least one pulverulent material, relative to the total weight of said composition.

3. The composition according to claim 1, wherein the aqueous phase to liquid fatty phase ratio is greater than 1.

4. The composition according to claim 1, wherein said volatile linear alkane comprises from 7 to 14 carbon atoms.

5. The composition according to claim 1, wherein the volatile linear alkane is chosen from n-heptane, n-octane, n-nonane, n-undecane, n-dodecane, n-tridecane, and n-tetradecane, and mixtures thereof.

6. The composition according to claim 1, wherein the volatile linear alkane is dodecane.

7. The composition according to claim 1, comprising at least two different volatile linear alkanes, differing from one another by a carbon number n of at least 1.

8. The composition according to claim 1, comprising a mixture of at least two volatile linear alkanes comprising:
   from 50% to 90% by weight of $C_n$ volatile linear alkane, with n ranging from 7 to 14,
   from 10% to 50% by weight of $C_{n+x}$ volatile linear alkane, with x greater than or equal to 1,
relative to the total weight of the alkanes in said mixture.

9. The composition according to claim 8, comprising an n-undecane:n-tridecane ($C_{11}/C_{13}$) mixture comprising:
   from 55% to 80% by weight of $C_{11}$ volatile linear alkane (n-undecane),
   from 20% to 45% by weight of $C_{13}$ volatile linear alkane (n-tridecane), relative to the total weight of the alkanes in said mixture.

10. The composition according to claim 1, comprising from 1% to 30% of volatile linear alkanes, by weight, relative to the total weight of said composition.

11. The composition according to claim 1, further comprising a non-emulsifying silicone elastomer.

12. The composition according to claim 1, further comprising at least one pulverulent material chosen from fillers, pigments, pearlescent agents, and mixtures thereof.

13. The composition according to claim 1, further comprising at least one surfactant chosen from a silicone surfactant, a polyglycerolated surfactant, and mixtures thereof.

14. The composition according to claim 1, wherein it is a foundation.

15. A process for making up and/or caring for a keratin material, comprising the application to said keratin material of the composition as defined in claim 1.

16. The composition of claim 1, wherein the emulsifying silicone elastomer is contained in an amount of from 0.1 to 20% by weight based on the total weight of the composition.

17. The composition of claim 1, wherein the emulsifying silicone elastomer is contained in an amount of from 0.5 to 5% by weight based on the total weight of the composition, and the volatile linear alkane is contained in an amount of from 3 to 10% by weight based on the total weight of the composition.

18. The composition of claim 1, which is stable after two months of storage.

19. The composition of claim 1, wherein said at least one emulsifying silicone elastomer is the sole silicone in the composition.

* * * * *